(12) United States Patent
Fukuchi

(10) Patent No.: US 6,329,419 B1
(45) Date of Patent: Dec. 11, 2001

(54) INSECTICIDAL AND MITICIDAL COMPOSITIONS

(75) Inventor: Toshiki Fukuchi, Yokohama (JP)

(73) Assignee: American Cyanamid Co., Madison, NJ (US)

(*) Notice: Subject to any disclaimer, the term of this patent is extended or adjusted under 35 U.S.C. 154(b) by 0 days.

(21) Appl. No.: 09/319,480

(22) PCT Filed: Dec. 8, 1997

(86) PCT No.: PCT/JP97/04498

§ 371 Date: Jun. 1, 1999

§ 102(e) Date: Jun. 1, 1999

(87) PCT Pub. No.: WO98/25462

PCT Pub. Date: Jun. 18, 1998

(30) Foreign Application Priority Data

Dec. 11, 1996 (JP) .................................................. 8-330867

(51) Int. Cl.$^7$ .......................... A01N 43/36; A01N 43/30; A01N 47/10

(52) U.S. Cl. .......................... 514/427; 514/465; 514/478; 514/479

(58) Field of Search ..................................... 514/427, 479, 514/465, 478

(56) References Cited

FOREIGN PATENT DOCUMENTS

771526-A2    5/1997    (EP) .

OTHER PUBLICATIONS

Tomlin, "The Pesticide Manual Incorporating The Agrochemicals Handbook", 10$^{th}$ Ed. (1995) pp. 437 and 438.*
J. R. Whitehead et al: "Performance of Pirate, Insecticide–Miticide, Against Cotton Pests in the Mid–South in 1992" Proceedings. Beltwide Cotton Conf., vol. 2, 1993, pp. 832–834, XP000617056, table 3.

* cited by examiner

*Primary Examiner*—Allen J. Robinson
(74) *Attorney, Agent, or Firm*—Barbara V. Maurer

(57) ABSTRACT

This invention relates to an insecticidal and miticidal composition which contains as active ingredients chlorfenapyr [4-bromo-2-(chlorophenyl)-1-(ethoxymethyl)-5-(trifluoromethyl)pyrrole-3-carbonitrile] in combination with asynergistic amount of at least one of a carbamate-type insecticidal compound.

12 Claims, No Drawings

INSECTICIDAL AND MITICIDAL COMPOSITIONS

This application is a 371 of PCT/JP97/04498, filed Dec. 8, 1997.

FIELD OF THE INVENTION

This invention relates to insecticidal and miticidal compositions which can be effectively applied in the agrohorticultural field. In more detail, it relates to insecticidal and miticidal compositions which contain two or more active ingredients and are especially effective against pest and mites which have acquired resistance to commercial insecticidal and miticidal agents.

BACKGROUND OF THE INVENTION

4-Bromo-2-(4-chlorophenyl)-1-(ethoxymethyl)-5-(trifluoromethyl)pyrrole-3-carbonitrile (hereinafter referred to as chlorfenapyr), which is an active ingredient of the insecticidal and miticidal composition of the invention, is known to be effective against insects such as Hemiptera pests such as leafhoppers (*Dolto cephalidae*), Lepidoptera pests such as diamond back moth (*Plutella xylostella*), common cutworm (*Spodoptera litura*) and apple leafminer (*Phyllonorycter ringoniella*) and Thysanoptera pests such as Thrips palmi and yellow tea thrips (*Spirtothrips dorsalis*) and agrohorticultural pests such as mites such as two-spotted spider mite (*Tetranychus urticae koch*). Kanzawa spider mite (*Tetranychus kanzawai kishida*) and *Aculops pelekassi* [Japanese Laid-open (Kokai) Patent Publication No. 104042/89].

The second active ingredient of the insecticidal and miticidal composition of the invention includes at least one of the carbamate-type compounds which are known to be effective insecticidal agents against agricultural pests such as Hemiptera, Lepidoptera and Coleoptera insects and mites.

Although insecticidal and miticidal agents have been developed in order to control various pests such as agrohorticultural pests or hygienic pests and in practice have been used as a single or a mixed agent, pests which have acquired resistance against various agents have been appearing as a result or the repeated use of these agents.

In particular, important economic pests in agrohorticulture such as spider mites (Tetranychidae), which have a propensity to easily develop resistance against pesticidal agents due to their ability to deposit large numbers of eggs and produce large numbers of generations which, themselves, require only a few days for development are of great concern. Resistance development in this pest family is also favored by a high mutation rate and frequent inbreeding, due to minimal migration. For these reasons, two-spotted spider mite (*Tetranychus urticae koch*), Kanzawa spider mite (*Tetranychus kanzawai kishida*), *Aculops pelekassi*, and the like have acquired resistance, to some degree, against almost all existing pesticidal agents. Therefore, in order to prevent and control the damage caused by spider mites, development of a new insecticidal and miticidal agent which shows a high effect against spider mites which have acquired resistance against the conventional miticidal agents is highly desirable.

However, to obtain an insecticidal and miticidal composition which shows no cross-resistance with existing insecticidal and miticidal agents, has no toxicity problems and has little negative impact on the environment, is extremely difficult. Therefore, a means to delay or prevent the development of resistant strains of pest species is always being sought. In order to apply an effective agent as long as possible, a rotational application of agents with different mechanisms of action is adopted for good pest management practice. However, this approach does not necessarily give satisfactory pest control. Therefore, after a resistance problem has occurred, a countermeasure to resistance by combining insecticidal and miticidal agents has been studied. However, a high synergistic action has not always been found.

Therefore, it is an object of this invention to provide an insecticidal and miticidal composition which demonstrates a high controlling effect even against spider mites which have acquired resistance against chlorfenapyr.

SUMMARY OF THE INVENTION

In order to establish a countermeasure to a resistance problem in spider mites against chlorfenapyr before such a problem occurs, the synergistic action with the existing insecticidal, miticidal and fungicidal agents was studied using resistant species which have been artificially established in the laboratory by selecting spider mites which have been treated with chlorfenapyr. Thus, it has now been found that an insecticidal and miticidal composition which contains as active ingredient chlorfenapyr in combination with at least one of the carbamate-type insecticidal ingredients shows a joint action or synergistic effect which could not be foreseen from each individual ingredient alone.

DETAILED DESCRIPTION OF THE INVENTION

The insecticidal and miticidal composition of the invention is particularly effective for the control of spider mites such as two-spotted spider mite (*Tetranychus urticae koch*), *Tetranychus cinnabarinus* (Boisduval), Kanzawa spider mite (*Tetranychus Kanzawai kishida*), hawthorn spider mite (*Tetranychus viennensis zacher*), and the like.

Advantageously, the insecticidal and miticidal composition of the invention shows not only a synergistic miticidal effect against the above-mentioned spider mites, but also demonstrates simultaneous control of troublesome pests such as leafroller moths (Tortricidae), Carposinidae, leafminer moths (Lyonetiidae), plant bugs (Pentatomidae), aphids (Aphididae), leaf-hoppers (Deltociphalidae), thrips (Thripidae), diamond back moths (*Plutella xylostella*), *Mamestra brassicae*, leaf beetles (Chrysomelidae), whiteflies (Aleyrodidae) and the like on important agronomic crops such as fruit trees, for example citrus, apple and pear; tea plants; vegetables and the like.

Chlorfenapyr, which is an active ingredient of the insecticidal and miticidal composition of the invention is a known compound described in Japanese Laid-open (Kokai) Patent Publication No. 104042/89 and its way of using as agrohorticultural insecticidal and miticidal agent is shown in the Publication. It can also be easily synthesized according to the method described in the Publication.

As carbamate-type insecticidal ingredients which are suitable for use as the second active ingredient in the composition of the invention, many compounds are known. For example, illustrative generic names and chemical names are listed hereinbelow. These examples, however, are not intended to limit the scope of the invention.

| Generic name: | Chemical name |
|---|---|
| BPMC: | 2-sec-Butylphenyl-N-methylcarbamate |
| MIPC: | 2-Isopropylphenyl-N-methylcarbamate |
| MTMC: | m-Tolyl-N-methylcarbamate |
| MPMC: | 3,4-Xylyl-N-methylcarbamate |
| NAC: | 1-Naphthyl-N-methylcarbamate |
| PHC: | 2-Isopropoxyphenyl-N-methylcarbamate |
| XMC: | 3,5-Xylyl-N-methylcarbamate |
| Alanycarb: | Ethyl(Z)-N-benzyl-N-{[methyl(1-methylthioethyli-deneaminoxycarbonyl)amino]thio}-β-alaninate |
| Ethiofencarb: | 2-(Ethylthiomethyl)phenyl methylcarbamate |
| Oxamyl: | Methyl-N, N'-dimethyl-N-[(methylcarbamoyl)oxy]-1-thioxamimidate |
| Carbosulfan: | 2,3-Dihydro-2,2-dimethyl-7-benzo[b]furanyl N-dibutyl-aminothio-N-methylcarbamate |
| Thiodicarb: | 3,7,9,13-Tetramethyl-5,11-dioxa-2,8,14-trithia-4,7,9,12-tetraazapentadeca-3,12-diene-6,10-dione |
| Pirimicarb: | 2-Dimethylamino-5,6-dimethylpyrimidin-4-yl dimethylcarbamate |
| Bendiocarb: | 2,2-Dimethyl-1,3-benzodioxol-4-yl methylcarbamate |
| Benfuracarb: | Ethyl N-[2,3-dihydro-2,2-dimethylbenzofuran-7-yloxycarbonyl(methyl)aminothio]-N-isopropyl-β-alaninate |
| Methomyl: | S-methyl-N-[(methylcarbamoyl)oxy]thioacetimidate |

The above-mentioned names of insecticidal agents are generic names described in "Agrochemicals Handbook 1992 Edition" published on Jul. 30, 1992 by Japan Plant Protection Association and "SHIBUYA INDEX -1996-(7th Edition)" published on Apr. 1, 1996 by ZENNOH.

In this invention, among the above-mentioned agents, especially 2-sec-butylphenyl-N-methyl-carbamate and 1-naphthyl-N-methylcarbamate are preferable due to a high synergistic action with chlorfenapyr.

For the preparation of the insecticidal and miticidal composition of the invention, it is suitable to formulate as a wettable powder, aqueous concentrate, emulsion, liquid concentrate, sol (flowable agent), powder, aerosol, or the like, by conventional methods such as admixing chlorfenapyr and publicly known carbamate-type insecticidal ingredient(s) with a suitable carrier and auxilliaries, such as emulsifiers, dispersants, stabilizers, suspending agents, penetrants, and the like.

The content of the total active ingredients of the composition of the invention, expressed as weight/weight %, is preferably in the range of about 1–90% for wettable powder, aqueous concentrate, emulsion, liquid concentrate and sol formulations. The preferable content of total active ingredients is about 0.5–10% for powder formulations and about 0.01–2% for aerosol formulations.

Carriers suitable for use in the insecticidal and miticidal compositions of the invention may be any solid or liquid carrier which is commonly used for an agrohorticultural composition. Various surfactants, stabilizers and other auxiliary ingredients may be used according to the necessity.

In commercially useful formulations, the composition of the invention may also be present in a mixture with other active agents, for example various insecticidal, miticidal, fungicidal and herbicidal agents, plant growth regulators, repellants, attractants, synergists and fertilizers and fragrances, in order to expand its applicability.

The ratio of chlorfenapyr to the publicly known carbamate-type insecticidal ingredient(s) in the insecticidal and miticidal composition of the invention is about 1 weight part of chlorfenapyr to about 0.01–100 weight parts, preferably about 0.5–20 weight parts, of a publicly known carbamate-type insecticidal ingredient(s).

Although the application amount may differ according to prevailing conditions such as the population density, the kinds and cultivation form of the target crop, the weather conditions, the manner of application, and the like, in general, the total amount of chlorfenapyr in combination with the publicly known carbamate-type insecticidal ingredient(s) is about 0.1–1,000 g, preferably about 40–500 g, per 10 ares. In actual practice, the composition of the invention when in the form of a wettable powder, aqueous concentrate, emulsion, liquid concentrate, sol, or the like may be diluted with water and applied to the crop at an application rate of about 100–700 liters per 10 ares. When the inventive composition is formulated as a powder or aerosol, the crop may be treated with the undiluted formulation.

The insecticidal and miticidal composition of the invention is further illustrated in the examples set forth hereinbelow. These examples are not intended to limit the scope of the invention. The parts all mean weight parts.

EXAMPLE 1

| FORMULATION EXAMPLE 1 EMULSION | |
|---|---|
| Clorfenapyr | 5 parts |
| BPMC | 40 parts |
| Xylene | 25 parts |
| Dimethyl formamide | 20 parts |
| Sorpol 3005X | 10 parts |
| (Polyoxyethylene type surfactant manufactured by Toho Chemical Industry Ltd., commercial name) | |

An emulsion is obtained by mixing homogeneously and dissolving the above-mentioned ingredients.

EXAMPLE 2

| FORMULATION EXAMPLE 2 WETTABLE POWDER | |
|---|---|
| Chlorfenapyr | 5 parts |
| NAC | 50 parts |
| Carplex #80 | 15 parts |
| (White carbon manufactured by Shionogi & Co., Ltd., commercial name) | |
| Zeeklite SP | 22 parts |
| (Mixture of kaolinite and cericite manufactured by Zeeklite Ind., commercial name) | |
| Calcium ligninsulfonate | 8 parts |

A wettable powder is obtained by homogeneously mixing the above-mentioned ingredients by jet air mill.

EXAMPLE 3

| FORMULATION EXAMPLE 3 SOL (FLOWABLE AGENT) | |
|---|---|
| Chlorfenapyr | 5 parts |
| NAC | 25 parts |
| Ethylene glycol | 8 parts |
| Sorpol AC3020 | 5 parts |
| (Toho Chemical Ind. Co., Ltd., commercial name) | |
| Xanthan gum | 0.1 parts |
| Water | 56.9 parts |

Chlorfenapyr, NAC and a previously prepared mixture of ethylene glycol, Sorpol AC3020 and xanthan gum are well mixed in water and dispersed. This slurry is then wet pulverized by Dynomill (Shinmaru Enterprises) to obtain a sol (flowable agent).

EXAMPLE 4

| FORMULATION EXAMPLE 4 POWDER | |
|---|---|
| Chlorfenapyr | 0.5 parts |
| BPMC | 3.5 parts |
| White carbon | 5 parts |
| Clay | 91 parts |
| (Nippon Talc Co., Ltd., commercial name) | |

The above-mentioned ingredients are homogeneously mixed and pulverized to obtain a powder Each of the above-prepared formulations is Suitable to be used as an agrochemical.

EXAMPLE 5

Test Example 1

In this experiment, the miticidal effect against female imagines (adults) of Kanzawa spider mite (*Tetranychus kanzawai kishida*) which are resistant to chlorfenapyr is evaluated.

Round leaf disks (2 cm diameter) are cut out of a first leaf of kidney bean by a leaf punch and 4 sheets of the disks are placed on wet sanitary cotton in a plastic cup (8 cm diameter). On each leaf disk, 4 female imagines of Kanzawa spider mite (*Tetranychus kanzawai kishida*) which had acquired a strong resistance to chlorfenapyr are inoculated.

After the inoculation, chlorfenapyr and a carbamate-type insecticidal agent(s) are dispersed in water containing 200 ppm of an extender (Sorpol 3005X manufactured by Toho Chemical Industry Ltd.) and diluted such that a predetermined concentration of active ingredient is obtained. Each plastic cup is sprayed with 3.5 ml of a test solution with a rotary spray tower (Mizuho Scientific Co., Ltd.) and stored in a constant temperature chamber held at 25±1° C. (32 individuals are tested per concentration, 4–5 concentrations are evaluated per formulation and 2 performances are repeated). Two days after treatment, the number of living and dead female imagines of Kanzawa spider mite (*Tetranychus kanzawai kishida*) which had acquired a strong resistance to chlorfenapyr is counted and the mortality (%) is calculated according to the formula shown hereinbelow.

$$\text{Mortality (\%)} = \frac{\text{Number of dead mite}}{\text{Number of living mite} + \text{Number of dead mite}} \times 100$$

Using these data, the $LC_{50}$ values are obtained by conventional probit analysis techniques. A co-toxi-city coefficient is calculated by applying Sun and Johnson's formula (J. Econ. Ent., Vol 53, p. 887, 1960) which is generally used to determine the degree of synergistic activity.

The $LC_{50}$ value of each individual effective ingredient which constitutes the insecticidal and miticidal composition of the invention is shown in Table I. The $LC_{50}$ values and the co-toxicity coefficients of the composition of the invention are shown in Table II.

$$\text{Co-toxicity coefficient} = T^c$$

$$T^c = \frac{\text{Actual toxicity index of mixture}}{\text{Theoretical toxicity index of mixture}} \times 100$$

For $T^c$ values greater than 100, the greater value indicates a stronger synergistic action. For a $T^c$ value equal to 100, an additive action is indicated. For $T^c$ values less than 100, the lesser value indicates a greater antagonistic action. A more detailed description of the calculation or the co-toxicity coefficient using the above-referenced Sun and Johnson formula follows.

The $LC_{50}$ values of Test Compound A alone and Test Compound B alone and the $LC_{50}$ value of the (A+B) mixture M are determined.

Actual Toxicity Index of Mixture $M=M^{ti}$

Each $LC_{50}$ value of effective ingredient A and effective ingredient B and the $LC_{50}$ value of the mixture of A+B are used to determine the actual toxicity index as shown in the equation below.

$$M^{ti} = \frac{LC_{50} \text{ of } A}{LC_{50} \text{ of } M} \times 100$$

Theoretical Toxicity Index of Mixture $M=Th.M^{ti}$ $$Th.M^{ti} = \text{Toxicity index of } A \times \% A \text{ in } M + \text{Toxicity index of } B \times \% B \text{ in } M$$

Toxicity Index of $B=B^{ti}$ $$B^{ti} = \frac{LC_{50} \text{ of } A}{LC_{50} \text{ of } B} \times 100$$

Toxicity Index of $A=A^{ti}$ $A^{ti}=100$

TABLE I

Evaluation Of The Effect Of Test Compounds Against Female Imago Of Kanzawa Spider Mite Which Have Acquired Resistance Against Chlorfenapyr

| TEST COMPOUND | $LC_{50}$ (ppm) |
|---|---|
| Chlorfenapyr | 1500 |
| BPMC | 3200 |
| NAC | 2700 |
| Ethiofencarb | 2100 |

The tested mite was a female imago of the chlorfenapyr-resistant strain of Kanzawa spider mite which was obtained by a long artificial selection procedure against chlorfenapyr in a laboratory on a colony of Kanzawa spider mite which had been collected in the field. As the $LC_{50}$ value for chlorfenapyr against a susceptible strain of spider mite is about 5 ppm, this strain has developed about a 300-fold resistance to chlorfonapyr.

It is generally known that the effect of carbamate-type insecticidal agents against spider mites is weak, and all the tested carbamate-type insecticidal agents showed only low miticidal effects.

TABLE II

Evaluation Of The Effect Of Test Mixtures Against Female Imago Of Kanzawa Spider Mite Which Have Acquired Resistance Against Chlorfenapyr

| TEST MIXTURE | RATIO (Chlorfenapyr: carbamate) | $LC_{50}$ (ppm) | $T^c$ |
|---|---|---|---|
| Chlorfenapyr + BPMC | 1:10 | 310 | 940 |
| Chlorfenapyr + NAC | 1:10 | 480 | 520 |
| Chlorfenapyr + Ethiofencarb | 1:10 | 440 | 460 |

As can be seen from the data on Table II, the co-toxicity coefficient of the test mixtures is a value greater than 100, which is indicative of strong synergistic action between chlorphenapyr and BPMG, NAC or Ethiofencarb. Though the detailed mechanism of the synergistic action of the composition of the invention is not clear, it is estimated that the metabolic system (group of enzymes), with which the spider mites, which has developed resistance to chlorfenapyr, detoxifies and decomposes the compound, be inhibited by a carbamate-type insecticidal ingredient(s) to demonstrate such an action. Therefore, a second ingredient of the insecticial and miticidal composition is thought not to be limited to the carbamate-type insecticidal agents tested in the above-mentioned examples and the carbamate-type insecticidal agents concretely mentioned above.

What is claimed is:

1. An insecticidal and miticidal composition which contains as active ingredients
   (a) chlorfenapyr; and
   (b) a synergistic amount of at least one of a substituted phenylmethylcarbamate insecticidal compound.

2. The composition of claim 1 wherein the substituted phenylmethylcarbamate insecticidal compound is selected from the group consisting of fenobucarb, ethiofencarb, isoprocarb, metolcarb, xylylcarb, propoxur, carbaryl, 3,5-xylylmethycarbamate, and beniocarb.

3. The composition of claim 2 wherein the substituted phenylmethylcarbamate insecticidal compound is fenobucarb, ethiocarb or carbaryl.

4. The composition of claim 3 wherein the substituted phenylmethylcarbamate insecticidal compound is fenobucarb.

5. The composition of claim 1 wherein the chlorfenapyr is present in a ratio of about 1 weight part to about 0.01–100 weight parts of the substituted phenylmethylcarbamate, insecticidal compound(s).

6. The composition of claim 4 wherein the ratio is about 1 weight part of chlorfenapyr to about 0.5–20 weight parts of the substituted phenylmethylcarbamate compound(s).

7. A process for the preparation of a composition of claim 1 which comprises admixing the active ingredients with a agrohorticulturally acceptable solid or liquid carrier.

8. The process of claim 6 wherein the active ingredients comprise chlorfenapyr in combination with an insecticidally synergistic amount of fenobucarb, ethiocarb or carbaryl.

9. The process of claim 7 wherein the chlorfenapyr is present in a ratio of about 1 weight part to about 0.5–20 weight parts of at least one of fenobucarb, ethiocarb or carbaryl.

10. A method of controlling insecticidal or miticidal pests which have acquired resistance to 4-bromo-2-(4-chlorophenyl)-1-(ethoxymethyl)-5-(trifluoromethyl) pyrrole-3-carbonitrile at a locus which comprises applying to the locus an effective amount of an insecticidal and miticidal composition comprising as active ingredients synergistic amounts of 4-bromo-2-(4-chlorophenyl)-1-(ethoxymethyl)-5-(trifluoromethyl)pyrrole-3-carbonitrile and at least one insecticidal substituted phenylmethylcarbamate.

11. The method of claim 10 wherein insecticidal compound is selected from the group consisting of fenobucarb, ethiofencarb, isoprocarb, metolcarb, xylylcarb, propoxur, carbaryl, 3,5-xylyl methylcarbamate, and bendiocarb.

12. The method of claim 11 wherein the substituted phenylmethylcarbamate insecticidal compound is fenobucarb, ethiocarb or carbaryl.

* * * * *